United States Patent [19]

Hogg

[11] 3,940,691
[45] Feb. 24, 1976

[54] PARTICLE ANALYZER OF THE COULTER TYPE INCLUDING COINCIDENCE ERROR CORRECTION CIRCUITRY

[75] Inventor: Walter R. Hogg, Miami Lakes, Fla.

[73] Assignee: Coulter Electronics, Inc., Hialeah, Fla.

[22] Filed: Feb. 19, 1974

[21] Appl. No.: 443,428

[52] U.S. Cl............ 324/71 CP; 328/41; 235/92 PL
[51] Int. Cl.²......................................... G01N 27/00
[58] Field of Search............ 324/71 CP; 235/92 PL; 328/41

[56] References Cited
UNITED STATES PATENTS

| | | | |
|---|---|---|---|
| 3,209,130 | 9/1965 | Schmidt | 235/92 PL |
| 3,649,820 | 3/1972 | Totsuka et al. | 235/92 PL |
| 3,705,295 | 12/1972 | Betz | 235/92 PL |
| 3,737,633 | 6/1973 | Collineau | 324/71 CP |

*Primary Examiner*—Alfred E. Smith
*Assistant Examiner*—Rolf Hille
*Attorney, Agent, or Firm*—Silverman & Cass, Ltd.

[57] ABSTRACT

A particle analyzer of the Coulter type has at least one sensing zone arrangement for generating a first train of particle pulses having a first number of particle pulses in response to passage through the sensing zone of a sample containing a plurality of particles to be counted. Generating circuitry is provided for generating a second train of particle pulses having a second number of particle pulses based upon a second sample containing a plurality of particles, or a hypothetical second sample. The second sample has a specific relationship to the first sample defined by one of either the first and second sample volume ratios, the first and second sample dilution ratio and the sensing zone volume ratio. Circuitry coupled to the first sensing zone arrangement and the generating circuitry is operative to mathematically change the first number of particle pulses and mathematically change the second number of particle pulses in the first and second trains of pulses respectively, and is further operative to combine the changed number of first and second pulses in accordance with a particular mathematical formula for providing an error corrected particle pulse count.

19 Claims, 5 Drawing Figures

PARTICLE ANALYZER OF THE COULTER TYPE INCLUDING COINCIDENCE ERROR CORRECTION CIRCUITRY

CROSS-REFERENCE TO RELATED APPLICATIONS

This application is related to patent application Ser. No. 238,079 filed Mar. 27, 1972, entitled "METHODS AND APPARATUSES FOR CORRECTING COINCIDENCE COUNT INACCURACIES IN A COULTER TYPE OF PARTICLE ANALYZER", which is hereby incorporated by reference into this application.

BACKGROUND OF THE INVENTION

This invention is directed to particle counting apparatuses which provide a statistic correction to a detected train of particle derived count pulses, such that effective random coincidence inaccuracies of count do not induce ultimate counting error.

The particle counting apparatuses concerned employ particle sensing zones in which more than one particle might reside at any one time and thereby randomly generate a coincidence condition. This invention particularly is directed to, but not limited to the determination of nonelectrical properties, such as size and count of microscopic particles, by measuring electrical properties (Patent Office class 324-71NE).

Now well known in the art of electronic particle counting and analyzing is apparatus marketed primarily under the trademark "Coulter Counter". Such apparatus and portions thereof are disclosed in several U.S. Pat. Nos., for example 2,656,508; 2,985,830; and 3,259,842 (each in class 324-71). A significantly important portion of such Coulter type of apparatus is the minute scanning aperture or scanning ambit or sensing zone relative to or through which are to pass and be detected single particles at a rate often well in excess of one thousand per second. Because of the physical parameters of the scanning aperture, and particle concentration, there frequently results the coincidence of two particles in the scanning ambit. As a result, there is effectively detected and counted only one particle, not two.

Although such primary form of coincidence loss of count is random in time, it follows a statistically ascertainable form from which curves, tables, and formulae are obtainable. A relatively simple one of such formulae is: $N' = K N^2$ in which $N'=$ the total number of coincidences, i.e., the required addend; $k =$ a constant which relates primarily to the physical parameters of the scanning elements of the apparatus and $N =$ the detected number of particles, the augend. Accordingly, the true or corrected count $N_0$ will equal the sum of $N+N'$.

In the above noted copending U.S. application, Ser. No. 238,079, filed Mar. 27, 1972, methods and apparatus are disclosed for correcting coincidence count inaccuracies in a Coulter type of particle analyzer. In the crossreferenced patent application, it is stated that an error corrected particle pulse count can be obtained using the formula;

$$N_0 = N_R + K N_R^2 \tag{1}$$

wherein $N_0$ is the true or corrected count, $N_R$ is the raw count, and $K$ is a constant which relates primarily to the physical parameters of the scanning elements of the apparatus. The copending application further states that two formulas such as formula (1) above can be simultaneously solved yielding an equation for $N_0$ in terms of two related raw counts $N_1$ and $N_2$ only, thus eliminating $K$, a parameter which is difficult to ascertain. The equation for $N_0$, stated in terms of $N_1$ and $N_2$ only, is different for each way in which the two related counts $N_1$ and $N_2$ are developed. The two related counts are developed:

a. by passing a sample volume through different scanning apertures having a known difference in their critical volume relationship to obtain $N_1$ and $N_2$;

b. by passing a sample volume through different scanning apertures having the same critical volume and using one output as $N_1$ and the sum of the outputs as $N_2$;

c. by passing two different dilutions of known dilution relationship of the sample through a single scanning aperture to obtain $N_1$ and $N_2$;

d. by passing one sample through one scanning aperture to generate $N_1$ and, by use of delaying and adding $N_1$ to itself, to form $N_2$.

An equation for $N_0$ stated in terms of $N_1$ and $N_2$ only, is given in the copending application for each of these ways of developing $N_1$ and $N_2$.

The raw counts $N_1$ and $N_2$ developed using one of the above noted methods are accumulated in accumulators. When the counts have been accumulated, the total counts are used in one of the equations in order to yield the true or corrected count.

The disadvantage with the above noted method and apparatus is that the true or corrected count cannot be obtained until after both raw counts $N_1$ and $N_2$ have been completely accumulated. Furthermore, the equations used for obtaining the true count, and which are stated in terms of $N_1$ and $N_2$, are quite complicated. In order to quickly solve these equations the accumulated totals $N_1$ and $N_2$ must be fed to computational equipment such as a calculator or computer which can quickly compute the true or corrected count.

SUMMARY OF THE INVENTION

It is therefore an object of this invention to provide a particle counter of the Coulter type which continuously provides a total particle count compensated for coincidence error. Another object of this invention is to provide a particle counter of the Coulter type which does not require complex computational equipment such as a computer in order to provide a count which has been corrected for coincidence errors.

In practicing this invention a particle analyzer of the Coulter type is provided for automatically developing an error corrected pulse count in response to particle pulses which are subject to coincidence error. The particle counter includes at least one sensing zone arrangement for generating a first train of particle pulses, which includes a first number of particle pulses, in response to passage through the sensing zone of a first sample containing a plurality of particles to be counted. Generating circuitry will generate a second train of particle pulses, having a second number of particle pulses, based upon either a second sample containing a plurality of particles, or a hypothetical second sample containing a plurality of particles. The first and second samples have a specific relationship to one another defined by either the first and second sample volume, the first and second sample dilution ratio or the first and second sensing zone volume ratio. Electronic circuitry such as multiplier and divider circuitry are coupled to the first sensing zone arrangement and the generating circuitry for mathematically multiplying and dividing the first number of particle pulses in the first train, and the second number of particle pulses in the second pulse train. The electronic circuitry is further operative to combine the mathematically manipulated and changed first and second pulse trains, either by addition or subtraction of one of the first and second pulse trains from the other, in order to produce an error corrected particle pulse count. The multiplication, division, addition and subtraction performance by the electronic circuitry is determined in accordance with the solution of particular simultaneous equations.

DESCRIPTION OF THE PREFERRED EMBODIMENTS

As previously noted, a basic, well known equation for correcting coincidence count error in a Coulter type particle detector is:

$$N_0 = N_R + KN_R^2. \quad (1)$$

Wherein $N_0$ is the true or corrected count, $N_R$ is the raw count and $K$ is a constant which relates primarily to the physical parameters of the scanning elements of the apparatus.

It has been found equally true or correct to start with the equation $$N_0 = N_R (1 + KN_0) \quad (2)$$

where $N_0$ and $N_R$ are the same as in equation (1), and $K$, although different in value from the $K$ in equation (1), represents the same constant. This equation, although known for a number of years, was not used because $N_0$ was required to derive $N_0$. Equation (2) however can be solved for $N_0$ as follows $$N_0 = N_R/1-KN_R = N_R (1+KN_R + K^2N_R^2 + K^3N_R^3 +...)$$

Based upon long accumulated statistical data it is known that for all practical particle concentrations selected for passage through a Coulter type particle detector the quantity $KN_0$ is much less than 1. Consequently, $K^2N_0^2$, and the remaining higher order terms in the above expansion can be neglected yielding $$N_0 = N_R (1 + KN_R)$$

This equation is identical to equation (1) except for a slightly different value of $K$. This clearly shows that equation (2) is as true or correct as equation (1). Now rewriting equation (2) to solve for $N_R$ we have $$N_R = N_0/1 + KN_0 = N_0 (1 - KN_0 + K^2N_0^2 - K^3N_0^3 +...) \quad (3)$$

At this point, based upon long accumulated statistical data and information, it is known that for all practical particle concentrations selected for passage through a Coulter type particle detector the quantity $KN_0$ is much less than 1. Consequently, $K^2N_0^2$, and the remaining higher order terms in equation (3) can be neglected yielding the equation $$N_R = N_0 - KN_0^2. \quad (4)$$

Equation (4) states that the raw count is equal to the true count, minus a loss which is proportional to the square of the true count.

Figure 1:
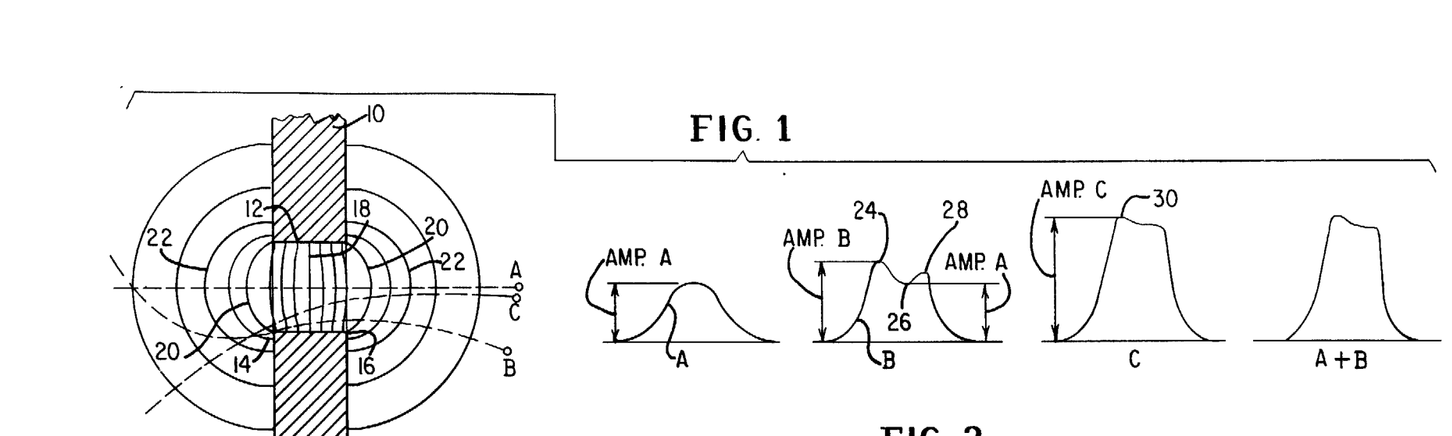
FIG. 1 is a diagrammatic view illustrating the profile of one form of scanning wafer having particles passing through its aperture along three different paths, with the resulting electric pulses being shown adjacent the aperture profile.

In FIG. 1, there is illustrated the sectional profile of a typical wafer 10 in a Coulter Counter counting and sizing apparatus having an aperture 12 therein. The structure is shown simply as a cylindrical bore with sharp edges 14 and 16. When aperture current is established by electrodes (not shown) on opposite sides of the wafer, electricity flows through the aperture from one side to the other, as for example from the left side to the right. The wafer 10 bearing the aperture 12 is immersed in the sample fluid or electrolyte, but no symbols are used to illustrate this in order to keep the view simple. As the electric current passes through the liquid, the electric current density within and adjacent the aperture is different than it is throughout other parts of the bodies of fluid through which the current passes. In the aperture itself, the electric current density will vary from location to location. The current density at the corners 14 and 16 will be much greater than anywhere elese.

Some of the isopotential lines representing the current density are illustrated in FIG. 1. These lines are shown to be perpendicular at every point where they touch the outer surface of the wafer 10, being transverse of the bore 12 at 18, slightly bulging out at the ends 20, and being quite arcuate at the outer surface of the bulge 22. Taken as a whole, the volume of fluid which is within as well as close to the physical limits of the aperture defines a volume that is effected by the concentration or degree of density of the electric current so as to define a "scanning ambit" or critical volume C.V. through which passing particles cause a resistive change and generate detectable pulses. Although the current density in the aperture 12 generally is greater than it is outside of the aperture, the current density is a maximum at the corners 14 and 16, where the electric current turns the corner, so to speak, to enter the aperture 12 and therefore, is greater than in the center of the aperture.

Digressing for a moment to further explain characteristics of pulses produced by passage of particles through aperture 12, consider now three particle paths A, B and C through the aperture from left to right along the broken lines shown in FIG. 1. The first particle A traverses approximately the center of the aperture with the physical stream of liquid and, as it passes from left to right through the influence of the increased current density, its maximum effect upon the resistance of the scanning ambit of the aperture is near the center of the aperture where the isopotential lines 18 are closest and parallel to each other. Considering the graph of the resulting electrical pulse, which may be assumed to have been made by some detecting means as will be discussed with reference to FIGS. 2–4, the pulse is shown as A, its maximum amplitude AMP.A is in its center, and is proportional to the size of the particle A. The duration of the pulse is equal to the time which the particle was within the ambit of the aperture, that is, within its electrical influence. This is considerably more than L, the length of the aperture 12, since, as noted, there is a convex bulge of relatively high electric current density outside of the geometric confines of the aperture.

If all particles follow paths similar to the path A, or quite close to the center of the aperture 12, then all of the resulting pulses would have the appearance of the pulse A, differing only in amplitude, which would be particle size related. It will be appreciated that the dimensions are exaggerated in the view to provide a better understanding of the theory of the discussion. The total duration of the pulse is commonly of the order of 20 to 40 microseconds.

All particles do not pass through the aperture 12 along paths similar to path A. Some approach along paths considerably displaced from the axis of the physical stream of liquid and are drawn into the aperture just before the stream enters the entrance to the aperture 12, as the path C, or even closer to the entrance, as the path B. Moreover, more than one particle can reside within and move through the scanning ambit at the same time or at least in overlapping times. For purposes of this discussion and the waveforms illustrated in FIG. 1, the particles A and B which traverse the paths A and B are to be assumed to be identical in size; whereas the particle C is twice that size and normally should have an amplitude AMP.C twice that of AMP.A, if it and particle A were to pass along the path A at different times. However, as the particle B moves through the ambit of the aperture 12, it passes close to the corner 14, where the current density is a maximum, and the effect is as though the resistance of the aperture 12 is increased at that point. Accordingly, there will be a peak 24 of amplitude AMP.B at the beginning of the pulse B.

As the particle B enters the aperture 12, it moves into the influence of the electric current region 18, where the density is quite uniform so that the corresponding amplitude of the pulse B will be that of AMP.A as shown in its part 26. As the particle B along the path B leaves the aperture 12, it passes close to the corner 16 through a region of high current density and, therefore, another peak 28 is generated, which would be larger than the part of the pulse indicated at 26.

The particle C, which is twice the size of particle A or B and therefore equal to the sum of their volumes, is shown traversing the path C, which produces the pulse C having a peak amplitude 30 which, while not twice that of the AMP.B of the peak 24 is more than twice AMP.A. The top of the pulse C is neither a smooth curved dome as that of pulse A, nor distinctly dual peaked, as in pulse B, nor are any of the pulses flat topped; hence, there is no single profile which can be used easily to distinguish a particle pulse generated by a single particle from a resulting waveform generated by the coincidence of two or more particles in the aperture ambit. This conclusion holds true, even though the pulse A profile is the most desirable, since coincident derived waveforms can have the profile of pulse A as well as pulse B or C, as next will be detailed with respect to the waveform A+B and also is developed with reference to waveforms in FIG. 5. Again it is to be understood that the above explanation is a digression providing background and understanding for problems associated with this invention.

If the particles A and B were to traverse the aperture ambit at the same time along their respective paths A and B, there would result the generation of a waveform or pulse A+B as shown in FIG. 1. Such pulse would be the point by point sum of the pulses A and B, as if plotted in a superimposed, well known manner. The striking similarity between the pulse C and the pulse A+B, though somewhat unique, leaves no doubt in the fact that two particles can and do create the electronic pulse image of only one particle even though of different size. Thus, in counting and size distribution studies accomplished by a Coulter Counter there will develop a loss of one particle count each time a pulse A+B is generated by the time coincidence of particles in the aperture.

The passage of the particles A and B need not be simultaneous to create a coincidence count loss. If two particles are slightly separated in time, there will be formed a dual peaked pulse, similar to the pulse B. Unfortunately, unless the valley 26 between the peaks 24 and 28 of a profile like pulse B is low enough to cross a low threshold, or the slopes are otherwise distinguishable, a simple threshold circuit is unable to distinguish between a pulse B derived from one or two particles and will report only one particle count; hence, a coincidence loss of one count.

With reference to equations (2) to (4), if the critical volume, C. V., or the scanning constant, K, could be ascertained, then the problem of coincidence errors would be resolved more easily and accurately than heretofor. Such is the goal of the method and apparatus according to FIGS. 2–4, which eliminates K and C.V. as unknowns.

Figure 2:
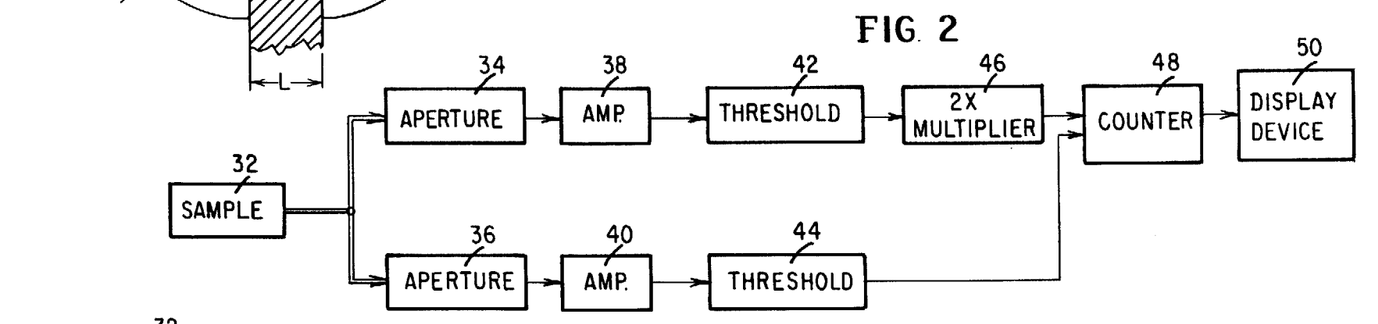
FIG. 2 is a block diagram of a particle analyzer according to one embidment of the invention.

With reference to FIG. 2, consider an arrangement in which a common source of particle sample 32 feeds into two aperture arrangements 34, 36, which respectively, apply their output pulses to amplifiers 38, 40, and threshold circuits 42, 44. Details of plural aperture setups are disclosed in U.S. Pat. Nos. 3,444,463, 3,444,464 and 3,549,994 (class 324-71). It is to be assumed herein that the aperture blocks contain not only the aperture wafer 10 and aperture 12, but also the aperture tubes, beakers, sample moving and measuring structures, electrodes, etc., all well known and disclosed in the patents cited herein.

If the particle analyzer is other than of the Coulter type, the blocks 34 and 36 will contain their appropriate sensing zone arrangements. Hence, the term aperture as used herein is not limiting.

For the first embodiment of the invention, consider the sensing zones or apertures in the blocks 34 and 36 of FIG. 2 to be of different volumes, with the aperture of 36 to be twice the critical volume of the aperture of 34. By substitution into equation (4):

$$N_1 = (1 - K_1 N_0) \text{ and} \quad (5)$$
$$N_2 = (1 - K_2 N_0) N_0, \quad (6)$$

wherein the uncorrected or raw count $N_R$ from the apertures 34 and 36 are, respectively $N_1$ and $N_2$, and their scanning constants are $K_1$ and $K_2$, respectively. Since we have chosen the ratio of their aperture volumes to be 1:2, for example, then $2K_1 = K_2$. By substitution into (5) and (6):

$$N_1 = (1 - K_1 N_0) N_0 \text{ and} \quad (7)$$
$$N_2 = (1 - 2K_1 N_0) N_0 \quad (8)$$

and by solving these simultaneous equations for $N_0$.

$$N_0 = 2N_1 - N_2. \quad (9)$$

Equation (9) does not contain any constants of calibration, nor does it depend upon knowledge of the critical volume per se. Furthermore, the mathematical function expressed by equation (9) can be easily implemented via electronic circuitry which can continuously process the particle pulses from the pulse trains representing the raw counts to provide a true or corrected count.

Referring again to FIG. 2, sample 32 when coupled to aperture 34 will cause a series of first pulses to be developed in response to passage of the particles in sample 32 through aperture 34. The series of first pulses forming a first pulse train and represented by $N_1$, are coupled from aperture 34 to amplifier 38. Amplifier 38 devlops amplified first pulses in response to the first pulses from aperture 34 and couples these amplified first pulses to threshold circuit 42. Threshold circuit 42 is of a commonly known type such that when the input signal exceeds a predetermined level, an output signal will be developed. The fixed amplitude output signal will have a duration equal to the duration that the input signal exceeded the predetermined threshold. For convenience, the pulses developed by threshold circuit 42 will be identified as first pulses.

The first pulses developed by threshold circuit 42 are coupled to a multiplier circuit 46. Multiplier circuit 46 is a times 2 multiplier. That is, for every first pulse coupled to multiplier circuit 46, it will develop 2 first pulses at its output. Multiplier circuit 46 then performs the $2N_1$ function in equation (9).

The first pulses developed by multiplier circuit 46 are coupled to counter 48. Counter 48 is an up-down counter. Each pulse coupled from multiplier circuit 46 will cause counter 48 to count up or in increasing numerical order, thereby accumulating or adding a continuous total amount of $2N_1$.

Sample 32 when coupled to aperture 36 will cause a series of second pulses to be developed in response to passage of the particles in sample 32 through aperture 36.

The series of second pulses, forming a second pulse train and represented by $N_2$, are coupled from aperture 36 to amplifier 40. It is to be understood of course that appropriate aperture excitation current is used and amplifier 40 has sufficient gain to compensate exactly for the reduced sensitivity of the larger aperture. Amplifier 40 develops amplified second pulses in response to the second pulses from aperture 36 and couples these amplified second pulses to threshold circuit 44. Threshold circuit 44 is identical to threshold circuit 42 and, as described with reference to threshold circuit 42, will develop second pulses in response to the second pulses coupled to threshold circuit 42 which exceeds a predetermined amplitude.

The second pulses developed by threshold circuit 44 are coupled to a second input of counter 48. The second input of counter 48 is a down-count input. Each pulse coupled from threshold circuit 44 will cause counter 48 to count down or in decreasing numerical order thereby continuously subtracting $N_2$ from the accumulated total in counter 48. The count shown by counter 48 at any particular instant in time is therefore the true or corrected count $N_0$ shown in formula (9) if the flow rates through the two apertures are adjusted to be equal.

The count accumulated by counter 48 at any instant of time may be coupled to display device 50 which can be either a visual readout or a printer. Display device 50 can provide a continuous readout of the corrected accumulated total count, or can provide such a readout upon request.

It will be appreciated that the volume ratio determines the numeric multipliers in equation (9). If, for example, the ratio was 1:5 rather than 1:2, the multiplier 5 would replace the value of 2 such that $5K_1 = K_2$.

Notwithstanding the fact that the apertures 34 and 36 have two different critical volumes, the same amount of sample is to flow through each; hence, the true count of the particles passing therethrough should be the same for each aperture, were it not for the coincidence phenomenon, which operates differently upon the apertures because of their differences in C.V. and K.

In the embodiment described with reference to FIG. 2, there is the assumption that apertures having known relationships with respect to their critical volumes are obtainable; whereas, it is also a basic premise of the problem that the actual volume, and therefore the critical volume of an aperture is not easily ascertainable. The named assumption is not rendered impossible or even impractical by the named premise, since one does not have to ascertain the actual volumes to be able to empirically construct two apertures having a known ratio of their (unknown) volumes. Nevertheless, the use of two apertures and two parallel channels of components presents cost, space, maintenance and other considerations which would be reduced if only one aperture were needed. Such is accomplished in the next described embodiments of FIGS. 3 and 4.

Figure 3:
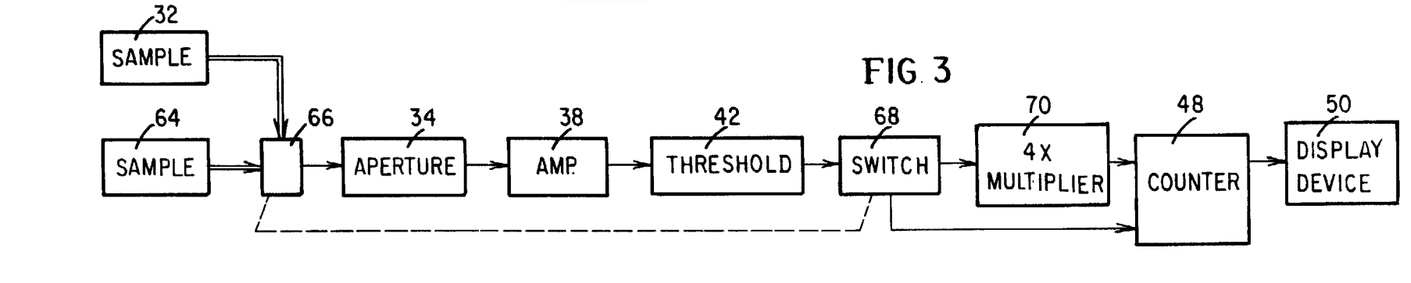
FIG. 3 is a block diagram of another embodiment of the invention.

With reference to FIG. 3, the aperture 34, amplifier 38, threshold circuit 42, counter 48 and display device 50 can be the same as those same named elements of FIG. 2. In this embodiment, the sample input arrangement provides for two different dilutions of the same sample and of a known dilution ratio. The two dilutions only are diagrammmatically shown in two containers 32 and 64 and their method of formation can be by any manner by which their relative dilutions can be ascertained. For example, the sample 32 can be analyzed and returned to the "container" 32 and there be diluted to become the sample 64.

For the description herein, it is assumed that the sample dilutions are 1:2, with the sample 64 that produces the raw count $N_2$ having been diluted by a factor of 2 from the sample 32 producing the raw count $N_1$. Suitable fluid flow control means 66 will determine which sample is being received by the aperture at any time and will ensure that equal amounts of the samples flow.

Since the same aperture is employed for both dilutions, the same scanning constant, $K$, is found in equations (10) through (13). Also, since the true count $N_0$ with respect to the sample 64 will be halved by the act of diluting the sample 64, the term $N_0/2$ will be employed in equation (11). By substitution into equation (4) again:

$$N_1 = N_0 - KN_0^2; \text{ and} \quad (10)$$
$$N_2 = N_0/2 - K(N_0/2)^2; \quad (11)$$

by multiplication.

$$4N_2 = 2N_0 - KN_0^2. \quad (12)$$

By subtraction of (10) from (11) and solving for $N_0$:
$$N_0 = 4N_2 - N_1. \quad (13)$$

The equation (13), just as equation (9), does not contain any constants of calibration, nor does it depend upon knowledge of the critical volume per se. The mathematical function expressed by equation (13) can be easily implemented via electronic circuitry which can continuously process the particle pulses from the pulse trains representing the raw counts to provide a true or corrected count.

Referring again to FIG. 3, in this example, the sample 64 that produces the raw count $N_2$ will be coupled through fluid control means 66 to aperture 34 first. This is done because formula (13) subtracts a quantity $N_1$ from a quantity $4N_2$. Assuming that $N_0$ is a positive number, the count of $4N_2$ should be accumulated first, unless of course counter 48 in FIG. 3 is capable of accumulating negative numbers. For the purposes of this example, counter 48 will be assumed to be capable of accumulating only positive numbers.

Fluid flow control means 66 upon actuation to allow sample 64 to flow to aperture 34 will also actuate switch 68, thereby coupling threshold circuit 42 to multiplier circuit 70. Sample 64 when coupled to aperture 34 will cause a series of second pulses to be developed in response to passage of the particles in sample 64 through aperture 34. The series of second pulses, forming a second pulse train and represented by $N_2$, are coupled from aperture 34 to amplifier 38. Amplifier 38 develops amplified second pulses in response to the second pulses from aperture 34 and couples these amplified pulses to threshold circuit 42. Threshold circuit 42 operates as previously described with reference to FIG. 2 to develop second pulses which are coupled from threshold circuit 42 through switch 68 to multiplier circuit 70.

Multiplier circuit 70 is a times 4 multiplier. That is, for every second pulse coupled to multiplier circuit 70, it will develop four second pulses at its output. Multiplier circuit 70 then performs the $4N_2$ function in equation (13). The quadrupled second pulses developed by multiplier 70 are coupled to counter 48 causing counter 48 to count up or in increasing numerical order thereby accumulating or adding a continuous total count of $4N_2$.

When the entire sample 64 has been coupled through aperture 34, fluid flow control means 66 is switched to allow sample 32 to be coupled to aperture 34. The switching of fluid flow control means 66 also causes switch 68 to couple the output of threshold circuit 42 to the second input of counter 48.

Sample 32 when coupled through fluid flow control means 66 to aperture 34 will cause the generation of a sequence of first pulses in response to passage of particles in sample 32 through aperture 34. The sequence of first pulses, forming a first pulse train and represented by $N_1$, are coupled from aperture 34 to amplifier 38 where they are amplified and coupled to threshold circuit 42. Threshold circuit 42 develops first pulses at its output in response to first pulses at its input exceeding a predetermined threshold and couples these first pulses through switch 68 to the second input of counter 48. Counter 48 will count down or in decreasing numerical order in response to each first pulse coupled thereto, thus subtracting $N_1$ from the accumulated total of $4N_2$. At the completion of passage of the entire sample 32 through aperture 34, a total corrected count $N_0$ will be counted by counter 48. This count may be coupled to display device 50 for display in any of the ways described with reference to FIG. 2.

Although the FIG. 3 embodiment is an improvement over the FIG. 2 embodiments, as earlier discussed, it possesses certain drawbacks. If the time and equipment necessary for making two precise dilutions and passing equal amounts of sample, and the time for processing the two dilutions sequentially could be eliminated there would be provided yet another significant improvement over the basic invention; such is accomplished by the embodiment of FIG. 4, in which the components having the same reference numbers as those in FIG. 2 can be employed.

Figure 4:
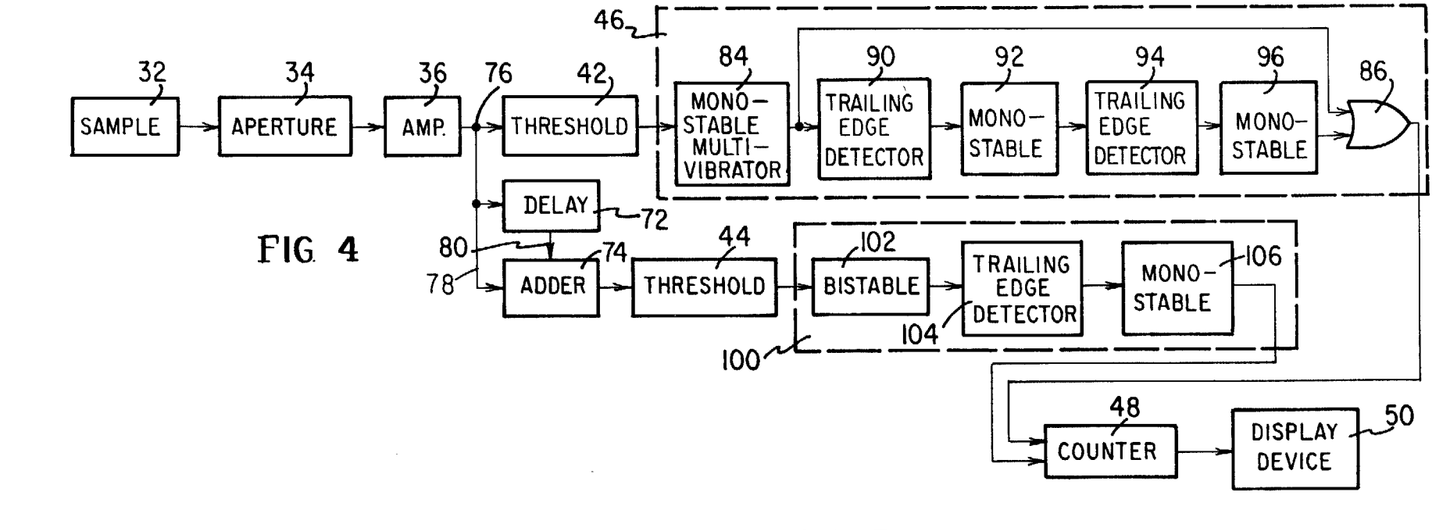
FIG. 4 is a block diagram of a preferred embodiment of the invention.

The process of the FIG. 4 embodiment operates upon the premise that a single sample 32 passing through only one aperture 34 can provide both of the raw counts $N_1$ and $N_2$. To accomplish such goal, one of the raw counts, $N_2$, is created artificially from the same particle pulse train that generates the count $N_1$. By using the same particle pulses for both $N_1$ and $N_2$, there will be less random variations between the two raw counts than if two apertures or two samples are employed. Effectively, the counts $N_1$ and $N_2$ represent two known dilutions with the stronger dilution being synthesized from the weaker dilution by an electronic delay device 72 and an adder circuit 74 being interposed between the aperture 34 and one threshold circuit 44 of the two parallel channel coupled threshold circuits.

Figure 5:
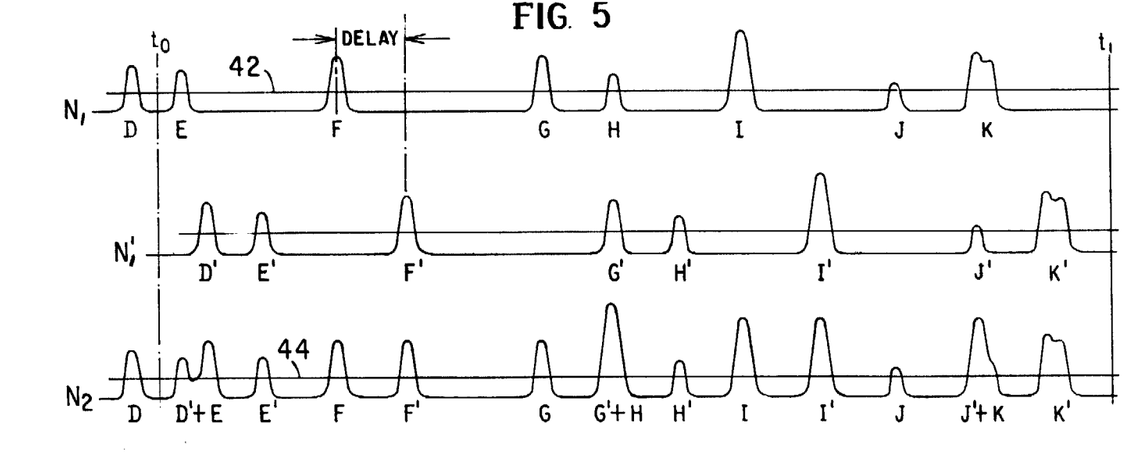
FIG. 5 is a plurality of graphs of representative particle pulses, for illustration of the invention according to the apparatus of FIG. 4.

As shown in FIGS. 4 and 5, output train $N_1$ of particle pulses D through K from the Coulter type aperture 34 is fed through the amplifier 36 to a junction point 76, from whence the entire train of particle pulses is applied on three separate paths to the threshold circuit 42, to the delay device 72, and directly to the adder circuit 74, the latter by an input line 78. The delayed train $N_1'$ of pulses D' through K' is applied from the delay circuit to the adder circuit by a line 80. The amount of delay is shown in FIG. 5 with reference to the time between the pulses F and F'. The delay duration can be arbitrarily chosen at almost any value greater than that which itself would create a coincidence error between a pulse and its own delayed counterpart, although it has been found that longer delay times, i.e., equal to or greater than the average spacing between particle pulses at higher particle concentrations, results in more accurate corrections.

Looking first at the train of pulses $N_1$, for simplicity all are shown to exceed the low threshold level 42 and thus are assumed to originate from particles of interest. However, the twin peaked pulse K appears to represent the not quite simultaneous passage of two particles and the large amplitude pulse I might represent the simultaneous passage of two small particles through the aperture 34. As shown, with respect to the pulse train $N_2$, the addition of $N_1$ and $N_1'$ forms the individual and unaltered pulses D, E', F, F', G, H'. I, I', J, and K', as well as the combined pulses D' + E, G' + H, and J' + k, each of which can be accumulated as a single particle pulse when its trailing edge crosses the threshold 44. Hence pulses D' and E can be counted separately; whereas, the pulses G' + H and J' + K produce coincidence lost counts, with the pulse J'+K probably being a synthetic triplet, i. e., two lost counts. The fact that the random spacing between pulses G and H equaled the delay time, caused the sum of G' and H to form a simultaneous coincidence pulse G' + H situation, like that of the pulse A + B in FIG. 1. Since the second pulse train and second pulse count $N_2$ is a synthesized double concentration count of $N_1$, the term $2N_0$ will be employed in equation (15). By substitution into equation (4) again;

$$N_1 = N_0 (1 - KN_0);  \qquad (14)$$
and
$$N_2 = 2N_0 (1 - 2KN_0);  \qquad (15)$$
by multiplication
$$N_2 = 2N_0 - 4KN_0^2 \cdot  \qquad (16)$$
Multiplying equation (14) by four.
$$4N_1 = 4N_0 - 4KN_0^2.  \qquad (17)$$
Subtracting equation (16) from equation (17) and solving for $N_0$.
$$N_0 = 2N_1 - N_2/2  \qquad (18)$$

Equation (18) can be easily implemented via electronic circuitry which can continuously process the particle pulses from the pulse trains representing the raw counts $N_1$ and $N_2$ to provide a true or corrected count. For a detailed discussion of the circuitry used to implement equation (18) reference is made to FIG. 4 and the following explanation.

Sample 32 when coupled to aperture 34 will cause a series of first pulses to be developed in response to passage of the particles in sample 32 through aperture 34. The series of first pulses, forming a first pulse train and identified by $N_1$, are coupled from aperture 34 to amplifier 36. Amplifier 36 amplifies the first pulses and couples them along three paths as previously explained. The amplified first pulses are coupled to threshold circuit 42. The second pulses in a second train synthesized as previously described by delay line 72 and adder 74, are coupled from adder circuit 74 to threshold circuit 44.

Threshold circuit 42 develops first pulses in response to the first pulses coupled thereto which exceed a predetermined amplitude, as described with reference to the circuit shown in FIG. 2. The first pulses developed by threshold circuit 42 are coupled to multiplier circuit 46 which is identical to multiplier circuit 46 shown and described with reference to FIG. 2. Although it is assumed that a times 2 multiplier circuit such as designated by multiplier circuit 46 is commonly known to those skilled in the art, a more detailed block diagram of the components making up such a multiplier is shown in FIG. 4.

Referring to times 2 multiplier 46, the first pulses coupled to multiplier circuit 46 are coupled to monostable multivibrator 84, which, in the preferred embodiment, may be a device commonly known in the art as a "one-shot". Monostable multivibrator 84 in response to each first pulse will develop an output pulse of predetermined amplitude and duration. In the preferred embodiment, monostable multivibrator 84 is a fast one-shot which develops a pulse of very short duration. The pulse developed by the monostable multivibrator 84 is coupled directly to one input of OR gate 86 via conductor 88, and to trailing edge detector 90. Trailing edge detector 90 responds to the termination of the pulse from monostable multivibrator 84, and particularly the trailing edge of the pulse from monostable multivibrator 84 to develop a pulse which is coupled to monostable multivibrator 92. Monostable 92 is identical to monostable 84 and will develop a pulse which is coupled to trailing edge detector 94. Trailing edge detector 94 is identical to trailing edge detector 90 and will develop a pulse in response to the trailing edge of the pulse from monostable 92 which is coupled to monostable multivibrator 96. Monostable multivibrator 96 is identical to monostables 84 and 92 and will develop a pulse which is coupled to the second input of OR gate 86. The purpose of trailing edge detectors 90 and 94, and monostables 92 and 96 is to develop a second pulse, identical to the pulse developed by monostable 84, but delayed in time such that it will not overlap any portion of the pulse developed by monostable multivibrator 84. The two pulses coupled to the inputs of OR gate 86 will cause OR gate 86 to actuate and develop 2 pulses at its output. For every first pulse coupled to the input of multiplier circuit 46, two first pulses are coupled from the output of multiplier circuit 46 to counter 48. The two first pulses developed by multiplier circuit 46 are counted by counter 48 as described with reference to FIG. 2 thereby adding or accumulating a continuous count of $2N_1$.

The second pulses in the second pulse train represented by $N_2$ are coupled from adder circuit 74 to threshold circuit 44. Threshold circuit 44 will develop second pulses in response to the second pulses coupled thereto which exceed a predetermined amplitude and couple these second pulses to divide by two circuit 100.

The second pulses coupled to divide by two circuit 100 are coupled to bistable multivibrator 102, which, in the preferred embodiment, is a bistable device of the type commonly referred to as a flip-flop. Bistable 102 will switch from a first to a second state in response to this second pulse. It will switch from the second back to the first state in response to a succeeding second pulse. The pulses developed by bistable 102 are coupled to trailing edge detector 104 which develops an output pulse in response to the trailing edge of each pulse developed by bistable 102. The output pulse developed by trailing edge detector 104 is coupled to monostable multivibrator 106. Monostable multivibrator 106 is identical to monostables 84, 92 and 96, and will develop an output pulse of predetermined amplitude and duration in response to each pulse from trailing edge detector 104. The output then of divide by two circuit 100, which has also the output of monostable 106 produces one-half the number of second pulses as are coupled to the input of divide by two circuit 100. Divide by two circuit 100 then performs the $N_2/2$ function in equation (18).

The second pulses developed by divide by two circuit 100 are coupled to the second input of counter 48. These pulses cause counter 48 to count down or in decreasing numerical order thereby subtracting the quantity $N_2/2$ from the quantity $2N_1$ in order to yield the true or corrected count $N_0$ as shown in formula (18). The count developed by counter 48 may be coupled to display device 50 for display in any manner previously described.

Although several specific formulas for $N_0$ have been presented hereinabove for various $N_1$ and $N_2$ origins and relationships, it is possible that other equally valid formulas for $N_0$ can be developed and then be applied with satisfactory results according to the apparatus of the invention claimed herein. Accordingly, the specific formulas are only examples of a broader or generic group of mathematic function relationships between $N_1$ and $N_2$ which can be employed within the scope of the invention.

Furthermore, it will be recognized by those skilled in the art that, although the invention is described in connection with the Coulter type of particle analyzer, it will apply equally well to any particle-counting apparatus which employs a sensing zone, whether this sensing zone is energized by an electric field, as in the Coulter Counter, or by light, acoustic energy, or a magnetic field.

What is sought to be protected by United States Letters Patent is claimed:

1. In a particle analyzer subject to coincidence errors in counting particle pulses, the combination including:
a first sensing zone arrangement for generating a first train of particle pulses having a first number of particle pulses in response to passage through said sensing zone of a sample containing a plurality of particles to be counted,
generating means for generating a second train of particle pulses having a second number of particle pulses and having a specific relationship to said first train of particle pulses defined by one of the sample volume, sample dilution and sensing zone volume for said first sensing zone arrangement, and
circuit means coupled to said first sensing zone arrangement and said generating means, for mathematically changing at least one of said first number of particle pulses in said first train of pulses and said second number of particle pulses in said second train of pulses, and second circuit means coupled to said first circuit means operative to accumulate said number of first and second particle pulses in said first and second trains of particle pulses for producing an error corrected particle pulse count.

2. The particle counter according to claim 1 wherein said generating means includes a second sensing zone arrangement having a particular critical volume which has a known ratio to the critical volume of the first sensing zone arrangement, said second zone arrangement being operative to generate said second train of particle pulses in response to passage of a second sample containing a plurality of particles to be counted through said second sensing zone, said second sample having a volume equal to said first sample.

3. The particle analyzer according to claim 1 wherein said generating means is coupled to said first sensing zone arrangement and operative to generate said second train of particle pulses in response to passage through said first sensing zone of a second sample containing a plurality of particles to be counted, said second sample having a known dilution ratio with respect to said first sample and a volume equal to said first sample.

4. The particle analyzer according to claim 1 wherein said generating means includes,
   delay circuit means coupled to said first sensing zone arrangement and operative in response to said first train of particle pulses to develop a time delayed first train of particle pulses, and
   summing means coupled to said delay circuit means and said first sensing zone arrangement for summing said first train of particle pulses and said time delayed first train of particle pulses coupled thereto to develop said second train of particle pulses.

5. In a particle analyzer subject to coincidence errors in counting particle pulses, the combination including:
   a first sensing zone arrangement for generating a first train of particle pulses having a first number of particle pulses in response to passage through said sensing zone of a sample containing a plurality of particles to be counted,
   generating means including a second sensing zone arrangement having a particular critical volume which has a known ratio to the critical volume of the first sensing zone arrangement, said second zone arrangement being operative to generate a second train of particle pulses in response to passage of a second sample containing a plurality of particles to be counted through said second sensing zone, said second sample having a volume equal to said first sample, and
   circuit means coupled to said first sensing zone arrangement and said generating means, said circuit means being operative to mathematically change said first and second number of pulses and accumulate said first and second number of pulses in accordance with the equation $$N_0 = \frac{aN_1 - N_2}{a - 1}$$

for producing an error corrected particle pulse count wherein $N_1$ is the number of first particle pulses in said first pulse train, $N_2$ is the number of second particle pulses in the second pulse train, a is the ratio of aperture size or aperture critical volume and $N_0$ is the error corrected particle pulse count.

6. The particle analyzer according to claim 5 wherein a, the ratio of aperture sizes or aperture critical volume is 2 and the equation is
   $$2N_1 - N_2 = N_0.$$

7. The particle analyzer according to claim 6 wherein said circuit means includes
   multiplier means coupled to said first sensing zone arrangement and operative to multiply said first number of particle pulses by a first particular number for producing said changed number of first particle pulses, and
   combiner circuit means coupled to said multiplier means and said generating means for accumulating said number of first and second pulses for producing said error corrected particle pulse count.

8. In a particle analyzer subject to coincidence errrors in counting particle pulses, the combination including:
   a first sensing zone arrangement for generating a first train of particle pulses having a first number of particle pulses in response to passage through said sensing zone of a sample containing a plurality of particles to be counted,
   generating means coupled to said first sensing zone arrangement and operative to generate said second train of particle pulses in response to passage through said first sensing zone of a second sample containing a plurality of particles to be counted, said second sample having a known dilution ratio with respect to said first sample and a volume equal to said first sample, and
   circuit means coupled to said first sensing zone arrangement and said generating means, said circuit means being operative to mathematically change said first and second number of pulses and accumulate said first and second number of pulses in accordance with the equation $$N_0 = \frac{a^2 N_2 - N_1}{a - 1}$$

for producing an error corrected particle pulse count wherein $N_1$ is the number of first particle pulses in said first train, $N_2$ is the number of second particle pulses in the second pulse train, a is the ratio of dilution between the two samples and $N_0$ is the error corrected particle pulse count.

9. The particle analyzer according to claim 8 wherein a, the ratio of dilution between the first and second sample is 2, and the equation is
   $$N_0 = 4N_2 - N_1.$$

10. The particle analyzer according to claim 9 wherein said circuit means includes,
   multiplier means coupled to said generating means and operative to multiply said second number of particle pulses by a second particular number for producing said changed number of second pulses, and
   combiner circuit means coupled to said multiplier means and said sensing zone arrangement for accumulating said number of first and second pulses for producing said error corrected particle pulse count.

11. In a particular analyzer subject to coincidence errors in counting particle pulses, the combination including:
- a first sensing zone arrangement for generating a first train of particle pulses having a first number of particle pulses in response to passage through said sensing zone of a sample containing a plurality of particles to be counted,
- generating means including delay circuit means coupled to said first sensing zone arrangement and operative in response to said first train of particle pulses, summing means coupled to said delay circuit means and said first sensing zone arrangement for summing said first train of particle and said time delayed first train of particle pulses coupled thereto to develop said second train of particle pulses, and
- circuit means coupled to said first sensing zone arrangement and said generating means, said circuit means being operative to mathematically change said first and second number of pulses and combine said changed first and second number of pulses in accordance with the equation $$N_0 = 2N_1 - (N_2 12)$$

for producing an error corrected particle pulse count, wherein $N_1$ is the number of first particle pulses in said first train, $N_2$ is the number of second particle pulses in the second train and $N_0$ is the error corrected particle pulse count.

12. The particle analyzer of claim 11, wherein said circuit means includes,
- first multiplier means coupled to said first sensing zone arrangement and operative to multiply said first number of particle pulses by a first particular number for producing said changed number of first pulses,
- second multiplier means coupled to said generating means and operative to multiply said second number of particle pulses by a second particular number for producing said changed number of second pulses, and
- combiner circuit means coupled to said first and second multiplier means for accumulating said changed number of first and second pulses for producing said error corrected particle pulse count.

13. The particle counter according to claim 12 wherein said combiner circuit means is a counter, said counter counting in increasing numerical order in response to said changed number of first pulses and in decreasing numerical order in response to said changed number of second pulses.

14. The particle counter according to claim 13 wherein said first multiplier means multiplies by 2 to produce 2 first pulses in response to each first pulse coupled thereto and said second multiplier means multiplies by one-half to produce 1 first pulse in response to every 2 first pulses coupled thereto.

15. In a particle analyzer subject to coincidence errors in counting particle pulses, the combination including:
- a first sensing zone arrangement for generating a first train of particle pulses having a first number of particle pulses in response to passage through said sensing zone of a sample containing a plurality of particles to be counted,
- generating means for generating a second train of particle pulses having a second number of particle pulses and having a specific relationship to said first train of particle pulses defined by one of the sample volume, sample dilution and sensing zone volume for said first sensing zone arrangement, and
- circuit means coupled to said first sensing zone arrangement and said generating means, said circuit means being operative to mathematically change said first and second number of pulses and combine said changed first and second number of pulses in accordance with the equation $$2N_1 - (N_2/2) = N_0$$

for producing an error corrected particle pulse count, wherein $N_1$ is the number of first particle pulses in said first train, $N_2$ is the number of second particle pulses in the second train and $N_0$ is the error corrected particle pulse count.

16. An apparatus for automatically developing an error corrected pulse count in response to first particle pulses which are subject to coincidence error including in combination:
- receiving means for receiving the first particle pulses,
- delay means coupled to said receiving means for delaying the first particle pulses,
- summing means coupled to said delay means and said receiving means for summing the first particle pulses and the delayed first particle pulses to develop second particle pulses,
- circuit means coupled to said summing means and said receiving means for mathematically changing at least one of the number of first pulses and the number of second pulses, and second circuit means coupled to said first circuit means operative to accumulate said number of first and second pulses for producing said error corrected pulse count.

17. The apparatus according to claim 16 wherein said circuit means includes,
- multiplier means coupled to said receiving means and operative to change the number of first pulses by developing a plurality of third pulses in response to each first pulse coupled thereto,
- divider means coupled to said summing means and operative to change the number of second pulses by developing a fourth particle pulse in response to a plurality of said second particle pulses coupled thereto, and
- said second circuit means include combiner circuit means coupled to said multiplier circuit means and said divider circuit means and operative to accumulate said third particle pulses and fourth particle pulses for producing said error corrected pulse count.

18. The apparatus according to claim 17 wherein said combiner circuit means is a counter, said counter counting in increasing numerical order in response to said third particle pulses and in decreasing numerical order in response to said fourth particle pulses.

19. The apparatus of claim 18 wherein said multiplier means multiplies by two to produce 2 third pulses in response to each first pulse coupled thereto and said divider means divides by two to produce 1 fourth pulse in response to every 2 second pulses coupled thereto.

* * * * *

UNITED STATES PATENT AND TRADEMARK OFFICE
CERTIFICATE OF CORRECTION

PATENT NO. : 3,940,691
DATED : February 24, 1976
INVENTOR(S) : Walter R. Hogg

It is certified that error appears in the above-identified patent and that said Letters Patent are hereby corrected as shown below:

Column 1, line 50, change "k" to -- K --.

Column 3, line 48, change "$N_R/1-KN_R$" to -- $N_R/(1-KN_R)$ --;

line 60, change "$N_O/1+KN_O$" to -- $N_R/(1+KN_O)$ --.

Column 4, line 5, change "Coulter Counter" to -- "Coulter Counter" --.

Column 6, line 2, change "Coulter Counter" to -- "Coulter Counter" --;

line 31, change "aperture" to -- "aperture" --;

lines 38-39, change "aperture" to -- "aperture" -- line 42, change "aperture" to -- "aperture" --;

line 43, change "aperture" to -- "aperture" --.

Column 7, line 63, change "5" (first occurrence) to -- "5" --;

line 63, change "2" to -- "2" --.

Column 10, line 38, change "combined" to -- "combined" --.

UNITED STATES PATENT AND TRADEMARK OFFICE
CERTIFICATE OF CORRECTION

PATENT NO. : 3,940,691
DATED : February 24, 1976
INVENTOR(S) : Walter R. Hogg

It is certified that error appears in the above-identified patent and that said Letters Patent are hereby corrected as shown below:

Column 11, line 34, change "fast one-shot" to

-- "fast one-shot" --.

Column 12, line 49, change "Coulter Counter" to

--"Coulter Counter" --.

Column 15, line 16, after "particle" insert -- pulses --.

line 26, change "$N_o$ 2N-($N_2$12)" to

-- $N_o = 2N_1 - \dfrac{N_2}{2}$ --;

line 32, after "11" omit the comma (,).

Signed and Sealed this

Twenty-sixth Day of April 1977

[SEAL]

Attest:

RUTH C. MASON
*Attesting Officer*

C. MARSHALL DANN
*Commissioner of Patents and Trademarks*